(12) United States Patent
Gordon et al.

(10) Patent No.: US 8,455,401 B2
(45) Date of Patent: Jun. 4, 2013

(54) METHODS AND DEVICES FOR MAKING ARRAYS

(75) Inventors: Steve Gordon, Weston, MA (US); Daniel Stetson, Stow, MA (US)

(73) Assignee: Intelligent Bio-Systems, Inc., Waltham, MA (US)

( * ) Notice: Subject to any disclaimer, the term of this patent is extended or adjusted under 35 U.S.C. 154(b) by 0 days.

(21) Appl. No.: 12/370,205

(22) Filed: Feb. 12, 2009

(65) Prior Publication Data

US 2009/0227471 A1 Sep. 10, 2009

Related U.S. Application Data

(60) Provisional application No. 61/029,778, filed on Feb. 19, 2008.

(51) Int. Cl.
*C40B 50/14* (2006.01)
*C40B 50/06* (2006.01)
*C40B 40/06* (2006.01)

(52) U.S. Cl.
USPC .................................. 506/30; 506/26; 506/16

(58) Field of Classification Search
None
See application file for complete search history.

(56) References Cited

U.S. PATENT DOCUMENTS

2003/0032046 A1* 2/2003 Duffy et al. ...................... 435/6

OTHER PUBLICATIONS

Adessi (Oct. 15, 2000 Nucleic Acids Research vol. 28 p. 1).*
Dressman (Jul. 11, 2003 PNAS USA vol. 100 p. 8817).*
Bio Rad (downloaded Dec. 7, 2009 from www.bio-rad.com) Frame Seal manual bulletin_03526.*
Bio Rad (downloaded Dec. 7, 2009 from www.bio-rad.com) Frame Seal catalog.*
Dressman, D. et al., "Transforming single DNA molecules into fluorescent magnetic particles for detection and enumeration of genetic variations", PNAS,100(15):8817-22(2003).
Ghadessy, F. et al., "Directed evolution of polymerase function by compartmentalized self replication", PNAS, 98(8): 4552-7 (2001).
Margulies, M. et al., "Genome sequencing in microfabricated high-density picolitre reactors", Nature, 437(15): 376-80 (2005).
Shendure, J. et al., "Accurate multiplex polony sequencing of an evolved bacterial genome", Science, 309: 1728-32 (2005).
Tawfik, D. et al., "Man-made cell-like compartments for molecular evolution", Nature Biotechnology, 16: 652-6 (1998).

* cited by examiner

*Primary Examiner* — Ardin Marschel
*Assistant Examiner* — Christian Boesen
(74) *Attorney, Agent, or Firm* — Medlen & Carroll, LLP

(57) ABSTRACT

The present invention relates to methods and devices for amplifying nucleic acid, and, in particular, amplifying so as to generate products on a surface without the use of emulsions. In a preferred embodiment, a plurality of groups of amplified product are generated on the surface, each group positioned in different (typically predetermined) locations on said surface so as to create an array.

11 Claims, 7 Drawing Sheets

METHODS AND DEVICES FOR MAKING ARRAYS

FIELD OF THE INVENTION

The present invention relates to methods and devices for amplifying nucleic acid, and, in particular, amplifying so as to generate products on a surface without the use of emulsions. In a preferred embodiment, a plurality of groups of amplified product are generated on the surface, each group positioned in different locations on said surface so as to create an array.

BACKGROUND

The use of water-in-oil emulsions was recently adapted to biological applications by several groups aiming at improving enzymes by directed evolution, SNP analysis on streptavidin coated beads, and DNA sequencing. Dressman et al., "Transforming single DNA molecules into fluorescent magnetic particles for detection and enumeration of genetic variations" Proc Natl Acad Sci USA, 100:8817-8822 (2003); Ghadessy et al., "Directed evolution of polymerase function by compartmentalized self replication" Proc Natl Acad Sci USA 98:4552-4557 (2001); Tawfik et al., "Man-made cell-like compartments for molecular evolution" 16:652-656 (1998); Margulies et al., "Genome sequencing in microfabricated high-density picolitre reactors" Nature 437:376-80 (2005); and Shendure et al., "Accurate multiplex polony sequencing of an evolved bacterial genome" Science 309: 1728-1732 (2005).

Unfortunately, the emulsion techniques are slow and cumbersome. As a result, they are not ideal for commercial applications.

SUMMARY OF THE INVENTION

The present invention relates to methods and devices for amplifying nucleic acid, and, in particular, amplifying so as to generate products on a surface without the use of emulsions. In a preferred embodiment, a plurality of groups of amplified product are generated on the surface, each group positioned in different (typically predetermined) locations on said surface so as to create an array. In one embodiment, each group is homogeneous. In one embodiment, each group consists of amplified product of a single nucleic acid template. In one embodiment, the method comprises performing limiting dilution PCR within closed compartments (e.g. sealed regions) created by two surfaces coming together.

In one embodiment, the present invention contemplates a method for making an array, comprising: a) providing: a first element comprising a first surface; a second element comprising a second surface; a plurality of indentations, wherein said indentations are on either said first surface or said second surface (or on both surfaces); and a solution comprising molecules selected from the group consisting of biomolecules and anchoring molecules; b) contacting said first surface with said solution under conditions such that at least a portion of said molecules attach to at least a portion of said first surface so as to create a modified surface comprising attached molecules; and c) positioning said second surface on top of said modified surface, so as to create a plurality of first regions defined by said indentations, said first regions comprising unmasked attached molecules, and second regions comprising masked attached molecules, thereby making an array. The present invention contemplates this embodiment of an array as a device.

It is not intended that the present invention be limited by the placement of the biomolecules and/or anchoring molecules. In one embodiment, said contacting of step b) causes the anchoring molecules to contact the indentations, the flat surface, or both. Similarly, the biomolecules may contact the indentations, the flat surface, or both.

In one embodiment, said positioning of step c) causes at least a portion of said solution on said first surface to move off of said first surface. In other words, bringing the surfaces into contact can cause liquid to be put under pressure so that some portion of the solution volume moves off (e.g. drains off and that portion of the volume is removed or lost). It is not intended that the present invention be limited to how the solution is brought into contact with the surface in step b). In one embodiment, the surface is dipped or immersed in the solution.

In one embodiment, said indentations have attached PCR primer(s) and said solution comprises nucleic acid template. In one embodiment, said template has been diluted to a concentration such that less than one hundred molecules on average (more preferably, less than 10, still more preferably, less than 1 molecule) of template are in contact with any one indentation. In one embodiment (e.g. where it is desired to have fewer empty wells), said template has been diluted to a concentration such that less than three on average—but more than 1 molecule—of template are in contact with any one indentation (or are within any one region). In one embodiment, said solution also contains reagents for PCR (e.g. polymerase, dNTPs, buffer, etc.). In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous.

It is not intended that the present invention be limited by the particular geometry of the surfaces. In one embodiment, said first surface is substantially flat (e.g. flat over 90% of the surface or comprising less than 10% deviation from flat). It can, but need not be, completely flat. It can be curved or only slightly curved. In one embodiment, said contacting of step b) results in substantially the entire first surface being contacted with said solution.

It is not intended that the present invention be limited by the nature of the surfaces. In one embodiment, said first surface comprises glass. In one embodiment, said first surface comprises a surface of a microscope slide. In one embodiment, said first surface comprises a surface of a microchip (e.g. a silicon surface). In a preferred embodiment, one or both surfaces comprise a polymer. The use of an elastomer is believed to enhance the sealing of one surface against the other.

It is not intended that the present invention be limited by the nature of the indentations. The term "indentation" as used herein, refers to a space, cavity, dent, crater, well, depression, hollow, recess or impression that is formed in the surface. In a preferred embodiment, indentations do not extend through the entire thickness of a surface. Useful dimensions for indentations are between 0.001 and 10,000 microns in diameter, with depths between $0.1\times$ and $10\times$ (i.e. 10 times) the diameter, and spacing (separation) of between $1\times$ and $3\times$ (i.e. three times) the diameter. Typically, indentations are between 50 nanometers and 50 microns in diameter, with depths approximately $0.5\times$ the diameter, and spacing approximately $1.2\times$ and $2\times$ (i.e. two times) the diameter. For example, in one embodiment, the present invention contemplates indentations of 50 nanometers in diameter, that are 25 nanometers deep, and that are spaced 60 nanometers apart. In another embodiment, the present invention contemplates indentations of 5 microns in diameter, which are 2.5 microns deep, and spaced 7 microns apart.

While a hole can be an indentation, the hole preferably does not extend completely through the surface. In a preferred embodiment, each of said indentations has a depth that extends up to the midpoint of said first or second element (i.e. the depth of the indentation is equal to or less than one-half the thickness of the surface). In one embodiment, said second surface is crenellated and the gaps comprise said indentations. In another embodiment, the indentations have raised edges. The term "raised edge" means that the edge of the indentation rises above the plane of the surface. In one embodiment, there are particles in the indentations (e.g. beads).

It is not intended that the present invention be limited by the manner in which the indentations are manufactured. In one embodiment, the indentations are introduced into the surface by treating the surface (e.g. etching a surface of glass, silicon or otherwise etchable surface). In another embodiment, the indentations are introduced by casting or molding. In a preferred embodiment, the indentations are integrally molded using a polymeric surface (e.g. plastic). The term "integrally molding" as used herein refers to the method of casting such that features are of unitary construction. The term "unitary construction" refers to an association of elements (e.g. the surface and the indentations) such that they are formed from the same piece of raw material without the need for further integration. In one embodiment, the first surface comprises plastic and has indentations. In one embodiment, said first surface is elastomeric.

In one embodiment, said indentations are evenly spaced. In one embodiment, said attached molecules after step b) are attached over substantially the entire first surface at a substantially even density. In another embodiment, the molecules are attached randomly over the surface or a portion of the surface.

It is not intended that the present invention be limited by the nature of the molecules. In one embodiment, said molecules are biomolecules. In a preferred embodiment, said biomolecules are nucleic acid molecules (e.g. oligonucleotides, polynucleotides, etc.). In a particularly preferred embodiment, said nucleic acid molecules comprise PCR primers. In another embodiment, said nucleic acid molecules comprise probes for RCA. In yet another embodiment, said nucleic acid molecules comprise hairpins (e.g. the hairpin allows the nucleic acid to self-prime in an extension reaction with a polymerase).

The present invention contemplates a variety of orientations for the two surfaces. The two surfaces can be placed on edge (e.g. two microscope slides, or a microscope slide and a cover, can be brought together so that each contacts the other on the broad flat surface, but then can be placed on edge) for purposes of detection in a device. In one embodiment, after step (c) said first surface faces up, and said second surface faces down.

In another embodiment, the present invention contemplates a method of amplifying nucleic acid template, comprising: a) providing: i) a first element comprising a first surface; ii) a second element comprising a second surface; iii) a plurality of indentations, wherein said indentations are on said first surface, second surface or both; iv) a first solution comprising a plurality of first PCR primers; v) a second solution comprising a plurality of second PCR primers; and vi) a third solution comprising template, polymerase, dNTPs and primers, wherein said primers are first PCR primers, second PCR primers or both; b) contacting said first surface with said first solution under conditions such that at least a portion of said first PCR primers attach to at least a portion of said surface so as to create a first modified surface comprising attached molecules; c) contacting said second surface with said second solution under conditions such that at least a portion of said second PCR primers attach to at least a portion of said bottom surface so as to create a second modified surface comprising attached molecules; and d) positioning said second modified surface on top of said first modified surface, so as to create a plurality of first regions defined by said indentations, said first regions comprising unmasked attached molecules, and second regions comprising masked attached molecules, thereby making an array. In one embodiment, said positioning of step d) causes at least a portion of said solution on said surface of said first element to move off of said surface. In one embodiment, each of said indentations has a depth that extends up to the midpoint between said bottom and top surfaces. In one embodiment, said second surface is crenellated and the gaps comprise said indentations. In one embodiment, said indentations are wells. In one embodiment, said first surface is substantially flat (10% or less deviation from flat). In one embodiment, said second surface comprises indentations. In one embodiments, said indentations comprise particles (e.g. beads). In one embodiment, said contacting of step b) results in substantially the entire surface being contacted with said solution. In one embodiment said indentations of said second surface element are evenly spaced. In one embodiment, said attached molecules after step b) are attached over substantially the entire surface at a substantially even density. In one embodiment, said first element comprises glass. In one embodiment, said first surface comprises plastic. In one embodiment, said first surface comprises indentations. In one embodiment, said indentations are formed at the time said plastic surface is molded. In one embodiment, said first surface is elastomeric. In one embodiment, said first element is a microscope slide. In one embodiment, said first element is a microchip. In one embodiment, said first PCR primers consist of forward PCR primers. In one embodiment, said first PCR primers consist of reverse PCR primers. In one embodiment, said second PCR primers consist of reverse PCR primers. In one embodiment, said second PCR primers consist of forward PCR primers.

In one embodiment of the above-described method, said template of said third solution has been diluted to a concentration such that less than one hundred molecules on average (more preferably, less than 10, still more preferably, less than 1 molecule) of template are in contact with any one indentation. In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. In one embodiment (e.g. where it is desired to have fewer empty wells), said template has been diluted to a concentration such that less than three on average—but more than 1 molecule—of template are in contact with any one indentation (or are within any one region). In such a case, the amplified product may not always be homogeneous (e.g. it may be the product of two different templates).

In yet another embodiment, the present invention contemplates a method of amplifying nucleic acid template, comprising: a) providing: i) a first element comprising a first surface; ii) a second element comprising a second surfaces; iii) a plurality of indentations, wherein said indentations are on said first surface, second surface or both; iv) a first solution comprising a plurality of first and second PCR primers; v) a second solution comprising template, polymerase, dNTPs and primers, wherein said primers are first PCR primers, second PCR primers or both; b) contacting said first surface with said first solution under conditions such that at least a portion of said PCR primers attach to at least a portion of said first surface so as to create a modified surface comprising attached molecules; and c) positioning said second surface on top of said modified surface, so as to create a plurality of first regions defined by said indentations, said first regions comprising unmasked attached molecules, and second regions comprising masked attached molecules, thereby making an array. In one embodiment, the method further comprises, prior to step c), contacting said modified surface with said second solution. In one embodiment, the method further comprises, after step c), contacting said modified surface with said second solution. In one embodiment of the above-described method, said template of said second solution has been diluted to a concentration such that less than one hundred molecules on average (more preferably, less than 10, still more preferably, less than 1 molecule) of template are in contact with any one indentation. In one embodiment of the above-described method, said template of said second solution has been diluted to a concentration such that less than one hundred molecules (more preferably, less than 10, still more preferably, less than 1 molecule) of template are in within any one region. In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. In one embodiment (e.g. where it is desired to have fewer empty wells), said template has been diluted to a concentration such that less than three on average—but more than 1 molecule—of template are in contact with any one indentation (or are within any one region). In such a case, the amplified product may not be homogeneous in every region where there is product.

In one embodiment, said positioning of step d) causes at least a portion of said second solution on said modified surface of said first element to move off of said surface. In one embodiment, said indentations are wells. In one embodiment, said indentations comprise particles (e.g. beads free or attached to wells). In one embodiment, said first surface is substantially flat. In one embodiment, said contacting of step b) results in substantially the entire first surface being contacted with said first solution. In one embodiment, said first surface comprises indentations. In one embodiment, said indentations are evenly spaced. In one embodiment, said attached molecules after step b) are attached over substantially the entire surface at a substantially even density. In one embodiment, said first element comprises glass. In one embodiment, said first element is a microscope slide. In one embodiment, said first surface comprises plastic. In one embodiment, said first surface comprises indentations. In one embodiment, said indentations are formed at the time said plastic surface is molded. In one embodiment, said first surface is elastomeric. In one embodiment, said first element is a microchip. In one embodiment, said first PCR primers consist of forward PCR primers. In one embodiment, said second PCR primers consist of reverse PCR primers. In one embodiment, the present invention contemplates the array created by the above-described method (as a composition). In one embodiment, the contacting prior to step c) is under conditions such that at least a portion of said template is amplified. In one embodiment, the contacting after step c) is under conditions such that at least a portion of said template is amplified. In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. In one embodiment, the method further comprises the step d) separating said first element from said second element.

In yet another embodiment, the present invention contemplates a method for making an array, comprising: a) providing: i) a first element comprising a first surface, said first surface comprising a plurality of indentations; ii) a second element comprising a second surface; iii) a third element; and iv) a solution comprising molecules selected from the group consisting of biomolecules and anchoring molecules; b) contacting said first surface with said solution under conditions such that at least a portion of said molecules attach to at least a portion of said first surface so as to create a modified surface comprising attached molecules; c) positioning said second surface on top of said modified surface, so as to create a plurality of first regions defined by said indentations, said first regions comprising unmasked attached molecules, and second regions comprising masked attached molecules, thereby making an array; and d) positioning said third element on top of said second element, thereby sandwiching said second element between said first element and said third element. In one embodiment, said second element is elastomeric. In one embodiment, said second element is a sheet of elastomer. In a preferred embodiment, said sheet is a film. In a particularly preferred embodiment, said molecules are PCR primers, in which case it is preferred that said solution comprises nucleic acid template and reagents for PCR (e.g. polymerase, dNTPs, buffer, etc.). In one embodiment of the above-described method, said template has been diluted to a concentration such that less than one hundred molecules on average (more preferably, less than 10, still more preferably, less than 1 molecule) of template are in contact with any one indentation. In one embodiment of the above-described method, said template of said second solution has been diluted to a concentration such that less than one hundred molecules (more preferably, less than 10, still more preferably, less than 1 molecule) of template are within any one region. In one embodiment (e.g. where it is desired to have fewer empty wells), said template has been diluted to a concentration such that less than three on average—but more than 1 molecule—of template are in contact with any one indentation (or are within any one region).

In one embodiment, the present invention contemplates a method for making an array, comprising: a) providing: a first element comprising a surface; a second element comprising bottom and top surfaces, said second element further comprising a plurality of channels extending from said bottom to said top surfaces; and a solution comprising molecules selected from the group consisting of biomolecules and anchoring molecules; b) contacting the surface of said first element with said solution under conditions such that at least a portion of said molecules attach to at least a portion of said surface (more preferably over the entire surface at a substantially even density) so as to create a modified surface comprising attached molecules; and c) positioning said bottom surface of said second element on top of said modified surface, so as to create first regions defined by said channels, said first regions comprising unmasked attached molecules, and second regions comprising masked attached molecules, thereby making an array. Importantly, the masking the above-described method differs from other masking processes in that the molecules are attached and thereafter masked (rather than using the mask to control where the molecules attach in the first place).

The present invention contemplates the array made by the above-described process. The present invention also contemplates the device comprising said first and second elements, as described above.

It is not intended that the present invention be limited to how the solution is brought into contact with the surface in step b). In one embodiment, the surface is dipped or immersed in the solution. In another embodiment, the solution is poured or pipetted onto the surface. In one embodiment, said positioning of step c) causes at least a portion of said solution (regardless of the manner by which it was introduced) on said surface of said first element to move off (or run off) of said surface. It is preferred that at least a portion of said solution remain on said surface after said positioning of step c).

In one embodiment, the method further comprises: d) providing a third element comprising a surface; and e) bringing the surface of said third element into contact with the top surface of said second element, thereby sandwiching said second element between the surfaces of said first and third elements, so as to create a device comprising sealed first regions. In one embodiment, the present invention contemplates this device, comprising first, second and third elements, said second element positioned between said first and third elements, said first element comprising masked and unmasked attached molecules.

It is not intended that the present invention be limited to the nature of the first, second or third elements. While these elements may be porous, it is preferred that they are non-porous. Importantly, the nature of each element may be different. In one embodiment, the first element is a membrane (e.g. nylon, nitrocellulose, etc.). In one embodiment, one or more elements are made from one or more polymers. For example, in a preferred embodiment, said second element comprises a polymer film.

In a preferred embodiment, said first and third elements are made from silicon, quartz or glass. For example, in a preferred embodiment, said first and third elements are glass plates. In a more preferred embodiment, said first and third elements are microscope slides. However, it is not intended that the present invention be limited to large surfaces. For example, in one embodiment, said first and third elements are microchips or silicon wafers.

It is not intended that the present invention be limited by the topography of the surfaces. In one embodiment, the surfaces may be flat or substantially flat (e.g. flat over 90% of the surface or comprising less than 10% deviation from flat). In another embodiment, the surfaces may be curved or raised (or partially curved or partially raised). In another embodiment, one or more surfaces may have depressions or protrusions. The depressions can take the form of wells or pits. The form of the protrusions can be of any type (e.g. conical or cylindrical shape and a cross-sectional configuration of a polygon, circle, ellipse or a combination thereof) and need not be identical. In an embodiment with protrusions, the protrusions may be identical in size and shape.

It is not intended that the present invention be limited to elements that are homogeneous. For example, crystalline silicon may not be the ideal material for biological compatibility. In one embodiment, it may be desirable to modify the surface with adsorbed surface agents, covalently bonded polymers, or a deposited silicon oxide layer. In one embodiment, deposition of a metal (e.g. gold) is contemplated. In one embodiment, deposition of a water-impermeable layer is contemplated on one or more elements. In a preferred embodiment, the impermeable layer is made by a sequence of three plasma enhanced vapor depositions: silicon oxide, silicon nitride, and silicon oxide.

Regardless of the material used, it may be desired in some embodiments to treat the surface. In one embodiment, the surface comprises an alkyne derivatized surface and said biomolecules are azido-labeled. In one embodiment, the surface is treated with a poly(ethylene glycol) such as a synthetic acridinyl poly(ethylene glycol) (APEG). In one embodiment, the surface is treated with protein such as BSA. In one embodiment, the surface is pretreated with a "hydrophilicity-enhancing compounds" which are those compounds or preparations that enhance the hydrophilicity of the surface. The definition is functional, rather than structural. For example, Rain-X anti-fog is a commercially available reagent containing glycols and siloxanes in ethyl alcohol. However, the fact that it renders a glass or silicon surface more hydrophilic is more important than the reagent's particular formula. In another embodiment, the surface (or portion thereof) is treated with a "hydrophobic reagents" which are compounds used to make "hydrophobic regions." It is not intended that the present invention be limited to particular hydrophobic reagents. In one embodiment, the present invention contemplates hydrophobic polymer molecules that can be grafted chemically to the silicon oxide surface. Such polymer molecules include, but are not limited to, polydimethylsiloxane. In another embodiment, the present invention contemplates the use of silanes to make hydrophobic regions, including but not limited to halogenated silanes and alkylsilanes. In this regard, it is not intended that the present invention be limited to particular silanes; the selection of the silane is only limited in a functional sense, i.e. that it render the surface hydrophobic. In one embodiment, the second element (or portion thereof) is dipped in a hydrophobic reagent prior to bringing it into contact with the surface of the first element, so as to create hydrophobic regions around hydrophilic regions defined by said channels. In one embodiment, n-octadecyltrichlorosilane (OTS) is used as a hydrophobic reagent. In another embodiment, octadecyldimethylchlorosilane is employed.

It is not intended that the present invention be limited by the size or shape of the channels of the second element, or the manner in which the channels of said second element are made. In one embodiment, the channels are etched. In a preferred embodiment, said second element comprises a polymer film treated with a laser to create said channels. While a variety of dimensions are possible, it is generally preferred that the regions defined by the channels have a width of between approximately 10 and 1000 µm (or greater if desired), and more preferably between approximately 100 and 500 µm. In a preferred embodiment, said channels are approximately 10-50 microns in diameter (most preferably 20 microns) and are spaced approximately 10-100 microns apart (most preferably 30 microns).

A variety of thermoplastic or elastomeric materials can be used for this purpose, such materials typically comprising one or more polymers. In one embodiment, polymers such as polyvinyl and polyurethane are employed. In one embodiment, polypropylene is employed. For example, polypropylene can be modified with amino groups by treatment with plasma in a mixture of nitrogen and hydrogen (1:2 V/V). Thereafter, using the method described above, oligonucleotides may be attached or synthesized in-situ. In another embodiment, polystyrene (e.g. a polystyrene thin film) is employed and amino-modified DNA is attached to the surface by reaction with succinimide ester groups bound to the polystyrenes. In yet another embodiment, polyethylenimine (PEI)

is used. In still another embodiment, said polymer comprises a polyimide. In still another embodiment, poly-methyl methacrylate (PMMA) is employed. In still another embodiment, polydimethylsiloxane (PDMS) material is employed. Mixtures of two or polymers may also be employed. Alternatively, an epoxy-based photosensitive resist (e.g. SU-8) may be used.

It is not intended that the present invention be limited by the nature of the biomolecules used in the above-described method. Biomolecules such as enzymes (e.g., polymerases, nucleases, etc.) and nucleic acids (both RNA and DNA) are contemplated. In addition, biomolecules such as proteins (e.g. antibodies) and lipids (e.g. glycosphingolipids) are contemplated. When nucleic acids are employed, the present invention contemplates oligonucleotides, primers (e.g. for PCR), probes (e.g. for RCA) and the like. In some embodiments, nucleic acids having particular designs (e.g. hairpins) are desired. In one embodiment of the above-described method, nucleic acid template is introduced into the device. In a preferred embodiment, said template has been diluted to a concentration such that less than one hundred molecules (more preferably, less than 10, still more preferably, less than 1 molecule) of template are in contact with any one channel. In a preferred embodiment, said template has been diluted to a concentration such that less than one hundred molecules on average (more preferably, less than 10, still more preferably, less than 1 molecule) of template are within any one region. In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. However, in one embodiment (e.g. where it is desired to have fewer empty channels), said template has been diluted to a concentration such that less than three on average—but more than 1 molecule—of template are in contact with any one channel (or are within any one region). In such a case, the amplified product within a region may not be homogeneous.

A variety of anchoring molecules can be used, including chemical moieties (epoxide groups, ester groups, amino groups, etc.) and biomolecules that function as anchoring molecules (e.g. biotin, avidin, etc.). Molecules function as anchoring molecules when they permit the attachment and immobilization of other molecules.

In another embodiment, the present invention contemplates a method for making an array, comprising: a) providing: a first element comprising a surface; a second element comprising bottom and top surfaces, said second element further comprising a plurality of channels extending from said bottom to said top surfaces; and a solution comprising forward and reverse PCR primers; b) positioning said bottom surface of said second element on top of said surface of said first element, so as to create unmasked regions defined by said channels, and masked regions; and c) contacting the surface of said first element with said solution under conditions such that at least a portion of said PCR primers attach to at least a portion of said surface so as to create a modified surface comprising attached molecules, said attached molecules positioned in said unmasked regions, thereby making an array. In one embodiment, said masked regions are free of attached molecules. In one embodiment, said contacting of step c) comprises introducing said solution into said channels. In one embodiment, said solution further comprises template, polymerase and dNTPs (or a second solution containing these components is introduced), and at least a portion of said PCR primers amplify at least a portion of said template. In a preferred embodiment, said template has been diluted to a concentration such that less than one hundred molecules on average (more preferably, less than 10, still more preferably, less than 1 molecule) of template are in contact with any one channel (or within any one unmasked region). In a preferred embodiment, the template amplified in any one unmasked region is homogeneous (i.e. only one type of template was amplified). In a preferred embodiment, different (diluted) template is introduced into at least two different unmasked regions such that each of said different template is simultaneously amplified and each of said amplified product is homogeneous. However, in one embodiment (e.g. where it is desired to have fewer empty channels), said template has been diluted to a concentration such that less than three on average—but more than 1 molecule—of template are in contact with any one channels (or are within any one region). In such a case, the amplified product may not be homogeneous in every instance.

In one embodiment, the method further comprises: providing a third element comprising a surface; and bringing the surface of said third element into contact with the top surface of said second element, thereby sandwiching said second element between the surfaces of said first and third elements, so as to create a device comprising sealed unmasked regions. In one embodiment, the present invention contemplates this device, comprising first, second and third elements, said second element positioned between said first and third elements, said first element comprising unmasked attached molecules.

Again, it is not intended that the present invention be limited by the nature or topography of the elements. In one embodiment, said first element is substantially flat, the bottom surface of said second element is substantially flat, and the surface of said third element is substantially flat. On the other hand, these surfaces may be curved or raised (or partially curved or raised), smooth or rough, with or without depressions or protrusions. In one embodiment, said first and third elements comprise glass (e.g. glass plates, microscope slides, etc.). In one embodiment, said first and third elements are microchips.

It is not intended that the present invention be limited by the dimensions or spacing of the channels. However, in one embodiment said channels of said second element are evenly spaced.

It is not intended that the present invention be limited to the extent a surface is covered with attached molecules. However, in one embodiment said attached molecules after step b) are attached over substantially the entire exposed surface at a substantially even density.

In a preferred embodiment, the present invention contemplates a method for making an array, comprising: a) providing: first and third elements each comprising a substantially flat surface; a second element comprising substantially flat bottom and top surfaces, said second element further comprising a plurality of substantially evenly spaced channels extending from said bottom to said top surfaces; and a solution comprising molecules selected from the group of biomolecules and anchoring molecules; b) contacting the substantially flat surface of said first element with said solution under conditions such that at least a portion of said molecules attach over substantially the entire surface at a substantially even density so as to create a modified surface comprising attached molecules; c) positioning said bottom surface of said second element on top of said modified surface, so as to create first regions defined by said channels, said first regions comprising unmasked attached molecules, and second regions comprising masked attached molecules, thereby making an array; and d) bringing the surface of said third element into contact with the top surface of said second element, thereby sandwiching said second element between the surfaces of said first and third elements, so as to create a device comprising sealed first regions. Again, the present invention contemplates the device created by the method described above, i.e. a device comprising first, second and third elements, said second element positioned between said first and third elements, said first element comprising attached molecules.

Again, it is not intended that the present invention be limited by the nature or topography of the elements. The surfaces may be smooth or rough, with or without depressions or protrusions. In one embodiment, said first and third elements comprise glass (e.g. glass plates, microscope slides, etc.). In one embodiment, said first and third elements are microchips. In one embodiment said second element comprises a polymer film (e.g. polyimide or other suitable polymer as discussed previously) treated (e.g. with a laser or by another process) to create said channels.

Again, it is not intended that the present invention be limited by the dimensions or spacing of the channels. However, in one embodiment said channels of said second element are evenly spaced. In one embodiment, said channels are approximately 10-50 microns (preferably 20 microns) in diameter and are spaced approximately 10-100 microns (preferably 30 microns) apart.

Again, it is not intended that the present invention be limited to the extent a surface is covered with attached molecules. However, in one embodiment said attached molecules after step b) are attached over substantially the entire exposed surface at a substantially even density.

Again, it is not intended that the present invention be limited by the nature of the anchoring molecules or biomolecules. Where said molecules are biomolecules, the preferred biomolecule comprises nucleic acid molecules. Particularly useful nucleic acid molecules include (but are not limited to) probes for rolling circle amplification (RCA), primers for PCR, and oligonucleotides for sequencing by synthesis. With regard to the latter, a preferred oligonucleotide comprises one or more hairpins. In one embodiment, template is introduced into the device (e.g. for amplification). In a preferred embodiment, said template has been diluted to a concentration such that less than one hundred molecules on average (more preferably, less than 10, still more preferably, less than 1 molecule) of template are in contact with any one channel (or within any one region). In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. However, in one embodiment (e.g. where it is desired to have fewer empty channels), said template has been diluted to a concentration such that less than three on average—but more than 1 molecule—of template are in contact with any one channel (or within any one region). In such a case, the amplified product may not be homogeneous in every instance.

The arrays described above are useful for a variety of tasks, including but not limited to amplification (including amplification done in advance of sequencing). In one embodiment, the present invention contemplates a method of amplifying nucleic acid template, comprising: a) providing: first and third elements, each comprising a surface; a second element comprising bottom and top surfaces, said second element further comprising a plurality of channels extending from said bottom to said top surfaces; a first solution comprising primers; and a second solution comprising template, polymerase and dNTPs; b) contacting at least a portion of said surface of said first element with said first solution under conditions such that at least a portion of said primers attach so as to create a modified surface comprising attached primers; c) positioning said bottom surface of said second element on top of said modified surface, so as to create first regions defined by said channels, said first regions comprising unmasked attached primers, and second regions comprising masked attached primers, thereby making an array; d) introducing said second solution into said first regions; e) bringing the surface of said third element into contact with the top surface of said second element, thereby sandwiching said second element between the surfaces of said first and third elements, so as to create sealed first regions of a device; and f) treating said sealed first regions under conditions such that said template is amplified. In one embodiment, said treating of step (f) comprises thermally cycling the device of step (e). In one embodiment, said first solution comprises forward primers for PCR. In one embodiment, said first solution further comprises reverse primers for PCR. In a preferred embodiment, said template has been diluted to a concentration such that less than one hundred molecules on average (more preferably, less than 10, still more preferably, less than 1 molecule) of template are in contact with any one channel (or within any one sealed region). In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. However, in one embodiment (e.g. where it is desired to have fewer empty regions), said template has been diluted to a concentration such that less than three on average—but more than 1 molecule—of template are within any one region. In such a case, the amplified product may not be homogeneous in every instance.

In one embodiment, said surfaces of said first and third elements are substantially flat. In one embodiment, said first and third elements comprise glass. In one embodiment, said first and second elements are microscope slides. In one embodiment, said first and second elements are microchips. In one embodiment, said third element comprises a polymer film treated with a laser to create said channels. In one embodiment, said channels are approximately 20 microns in diameter and are spaced approximately 30 microns apart. In one embodiment, the present invention contemplates the device (as a composition) with the elements assembled as described above.

In yet another embodiment, the present invention contemplates a method of amplifying nucleic acid template, comprising: a) providing: i) first and third elements, each comprising a surface; ii) a second element comprising bottom and top surfaces, said second element further comprising a plurality of channels extending from said bottom to said top surfaces; iii) a first solution comprising primers; and iv) a second solution comprising template, polymerase and dNTPs; b) positioning said bottom surface of said second element on top of said surface of said first element, so as to create unmasked regions defined by said channels, and masked regions; c) contacting at least a portion of said surface of said first element with said first solution under conditions such that at least a portion of said primers attach in said unmasked regions so as to create a modified surface comprising attached primers; d) introducing said second solution into said unmasked regions; e) bringing the surface of said third element into contact with the top surface of said second element, thereby sandwiching said second element between the surfaces of said first and third elements, so as to create sealed unmasked regions of a device; and f) treating said sealed first regions under conditions such that said template is amplified. In one embodiment, said treating of step (f) comprises thermally cycling the device of step (e). In one embodiment, said first solution comprises forward primers for PCR. In one embodiment, said first solution further comprises reverse primers for PCR. In a preferred embodiment, said template has been diluted to a concentration such that less than one hundred molecules on average (more preferably, less than 10, still more preferably, less than 1 molecule) of template are in contact with any one channel (or within any one sealed unmasked region). In a preferred embodiment, the template amplified in any one sealed unmasked region is homogeneous (i.e. only one type of template was amplified). In a preferred embodiment, different (diluted) template is introduced into at least two different sealed unmasked regions such that each of said different template is simultaneously amplified and each of said amplified product is homogeneous. However, in one embodiment (e.g. where it is desired to have fewer empty unmasked regions), said template has been diluted to a concentration such that less than three on average—but more than 1 molecule—of template are within any one unmasked region).

In one embodiment, said surfaces of said first and third elements are substantially flat. In one embodiment, said first and third elements comprise glass. In one embodiment, said first and second elements are microscope slides. In one embodiment, said first and second elements are microchips. In one embodiment, said third element comprises a polymer film treated with a laser to create said channels. In one embodiment, said channels are approximately 20 microns in diameter and are spaced approximately 30 microns apart. In one embodiment, the present invention contemplates the device with the elements assembled as described above.

In yet another embodiment, the present invention contemplates a method of amplifying nucleic acid template, comprising: a) providing: i) first and third elements, each comprising a surface; ii) a second element comprising bottom and top surfaces, said second element further comprising a plurality of channels extending from said bottom to said top surfaces; iii) a first solution comprising a plurality of forward PCR primers; iv) a second solution comprising a plurality of reverse PCR primers; and v) a third solution comprising template, polymerase and dNTPs; b) contacting at least a portion of said surface of said first element with said first solution under conditions such that at least a portion of said forward primers attach so as to create a first modified surface comprising attached forward primers; c) contacting at least a portion of said surface of said third element with said second solution under conditions such that at least a portion of said reverse primers attach so as to create a second modified surface comprising attached reverse primers; d) positioning said bottom surface of said second element on top of said first modified surface, so as to create first regions defined by said channels, said first regions comprising unmasked attached forward primers, and second regions comprising masked attached forward primers; e) introducing said second solution into said first regions; f) bringing said second modified surface into contact with the top surface of said second element, thereby sandwiching said second element between the modified surfaces of said first and third elements, so as to create sealed first regions of a device, said sealed first regions comprising unmasked attached forward and reverse primers; and g) treating said sealed first regions under conditions such that said template is amplified. In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. However, in one embodiment (e.g. where it is desired to have fewer empty channels), said template has been diluted to a concentration such that less than three on average—but more than 1 molecule—of template are in contact with any one channel (or are within any one region).

In one embodiment, said treating of step (g) comprises thermally cycling the device of step (f). In one embodiment, the present invention contemplates the device with the elements assembled as described above. In one embodiment, said first and third elements comprise glass. In one embodiment, said first and third elements are microscope slides. In one embodiment, said first and third elements are microchips. In one embodiment, said second element comprises a polymer film. In one embodiment, said polymer film is treated with a laser to create said channels.

In one embodiment, both the forward and reverse primers are attached to the same surface in the same or different concentrations. In this embodiment, amplification causes the generation of DNA strands attached to the surface by either the forward or reverse primer. In one embodiment, a separate sequencing primer is then used to determine the sequence of the forward single strands; then, a re-priming step with a different sequencing primer is used to determine the sequence of the reverse single strands. In this manner, one can get sequence information from both ends.

To maximize the efficiency of generating both forward and reverse strands on a solid surface, it is useful to have the amplification occur in two phases under different conditions. For high efficiency of solid-surface PCR, it is desirable to have only one of the two primers on the surface with the other primer in solution; thus, amplicons are forced to use the surface-bound primers and become attached. Such solid surface could be a surface of a chip or a surface of a microsphere or bead. The efficiency of the reaction is helped with the use of a limiting concentration of the bound primer in solution. In one embodiment, the supply of solution-based primers is regulated based on the reaction and/or structural conditions (i.e. melting temperature, hairpins, cleavable blocker, etc). For example, if one inhibits the annealing of solution-based reverse primers, but allow for the annealing of an abundance of solution-based forward primers, then we can drive the amplification of fragments that are only attached through the reverse primers on the solid surface (only reverse primers that are available are on the surface). However, if required, a small quantity of active reverse primer could added to improve efficiency. As this reaction progresses, the solution-based forward primers will be exhausted. During a second phase of the reaction, the solution-based (inactive) reverse primers will be activated by some means (change in temperature, removal of blocking group, etc) and amplification occurs with strands being attached through the forward primers affixed to the solid surface. Specific examples of primer activation could include, by are not limited to, a photocleavable blocking group or by changing the PCR annealing temperature allowing initially dormant reverse primers designed with or without hairpins to become active in the second phase of a PCR reaction.

In yet another embodiment, the present invention contemplates a method of amplifying nucleic acid template, comprising: a) providing i) a population of nucleic acid template molecules and ii) a plurality of regions, said regions defined by a plurality of indentations in a first surface, said first surface in contact with a second surface, wherein each of said regions comprises one or more PCR primers; and b) amplifying, in said regions, at least a portion of said population of nucleic acid template molecules. In a preferred embodiment, the template amplified in any one sealed region is homogeneous (i.e. only one type of template was amplified). In a preferred embodiment, different (diluted) template is introduced into at least two different sealed regions such that each of said different template is simultaneously amplified and each of said amplified product is homogeneous. However, in one embodiment (e.g. where it is desired to have fewer empty regions), said template has been diluted to a concentration such that less than three on average—but more than 1 molecule—of template are within any one region. In such a case, the amplified product may not be homogeneous but may be substantially homogeneous (i.e. the product of not more than three different templates).

In one embodiment, said PCR primers are attached to either said first surface or said second surface. In one embodiment, said amplifying in step b) is performed in a solution comprising said template molecules, one or more polymerases, and all four dNTPs. In one embodiment, said solution further comprises unattached PCR primers. In one embodiment, the concentration of said template molecules in said solution is such that there is less than one template molecule on average per region. In one embodiment, the concentration of said template molecules in said solution is such that there is greater than one template molecule on average per region. In one embodiment, the concentration of said template molecules in said solution is such that there are greater than two template molecules on average per region. In one embodiment, the concentration of said template molecules in said solution is such that there are not greater than three template molecules on average per region.

In yet another embodiment, the present invention contemplates a method of amplifying nucleic acid template, comprising: a) providing a population of nucleic acid template molecules and a device comprising a first surface comprising attached PCR primers in contact with a second surface comprising attached PCR primers, either said first surface or said second surface comprising a plurality of indentations, said indentations defining a plurality of regions, said regions comprising unmasked PCR primers; and b) amplifying at least a portion of said population of nucleic acid template molecules with said unmasked PCR primers in one or more of said regions. In one embodiment, said attached PCR primers of said first and second surfaces that are outside said regions are masked by said contact. In one embodiment, said amplifying in step b) is performed in a solution comprising said template molecules, one or more polymerases, and all four dNTPs. In one embodiment, said solution further comprises unattached PCR primers. In one embodiment, the concentration of said template molecules in said solution is such that there is less than one template molecule on average per region. In one embodiment, the concentration of said template molecules in said solution is such that there is greater than one template molecule on average per region. In one embodiment, the concentration of said template molecules in said solution is such that there are greater than two template molecules on average per region. In one embodiment, the concentration of said template molecules in said solution is such that there are not greater than three template molecules on average per region.

In one embodiment, the present invention contemplates a method, comprising: a) providing: I) a first element comprising a surface; ii) a second element comprising bottom and top surfaces, said bottom surface comprising a plurality of indentations; iii) a first solution comprising a plurality of first PCR primers; iv) a second solution comprising a plurality of second PCR primers; and v) a third solution comprising template at a known concentration; b) contacting the surface of said first element with said first solution under conditions such that at least a portion of said first PCR primers attach to at least a portion of said surface so as to create a first modified surface comprising attached molecules; c) contacting the bottom surface of said second element with said second solution under conditions such that at least a portion of said second PCR primers attach to at least a portion of said bottom surface so as to create a second modified surface comprising attached molecules; and positioning said second modified surface on top of said first modified surface, so as to create a plurality of first regions defined by said indentations, said first regions comprising unmasked attached molecules, and second regions comprising masked attached molecules, thereby making an array. In one embodiment, the method further comprises introducing said third solution to said array under conditions such that at least a portion of said template is amplified, wherein the known concentration is such that less than one template molecule is present on average in each of said plurality of first regions. In one embodiment, the method further comprises introducing said third solution to said array under conditions such that at least a portion of said template is amplified, wherein the known concentration is such that greater than one template molecule is present on average in each of said plurality of first regions. In one embodiment, the method further comprises introducing said third solution to said array under conditions such that at least a portion of said template is amplified, wherein the known concentration is such that greater than two template molecules are present on average in each of said plurality of first regions. In one embodiment, said introducing of said third solution is prior to step d). In one embodiment, said third solution further comprises at least one polymerase and all four dNTPs. In one embodiment, said third solution further comprises PCR primers. In one embodiment, the method further comprises the step e) separating said first element from said second element.

DESCRIPTION OF THE FIGURES

FIG. 1A shows the three elements of the device (a bottom piece, a top piece, and a middle piece) not yet combined. A solution (typically containing biomolecules, such as nucleic acid template and reagents for PCR) is shown positioned on the bottom piece such that fluid has entered the wells. FIG. 1B shows the assembled device wherein the middle piece (in this case, an elastomeric sheet) acts as a seal, trapping fluid in the wells. Where primers have been attached to the surface of the bottom piece prior to assembly, the middle piece will mask the primers on the surface interface, but leave the primers attached to the wells unmasked and functional for amplification. Because of the excess fluid, a portion of the solution positioned on the bottom surface typically runs off the bottom surface when the middle piece is applied and the device is assembled. After the device is used (e.g. nucleic acid within the wells is amplified by thermocycling the device, or portion thereof), it can be taken apart, resulting in the three separated elements.

2A shows the assembled device. Where primers have been attached to the surface of the bottom piece prior to assembly (as shown in 2A), the middle piece will mask the primers at the point of contact, but leave the primers in the channels unmasked and functional for amplification. After the device is used (e.g. nucleic acid template within the channels is amplified by thermocycling the device, or portion thereof), it can be taken apart (as shown in 2B), resulting in a surface comprising discrete regions comprising amplified product, i.e. an array.

Figure 3:
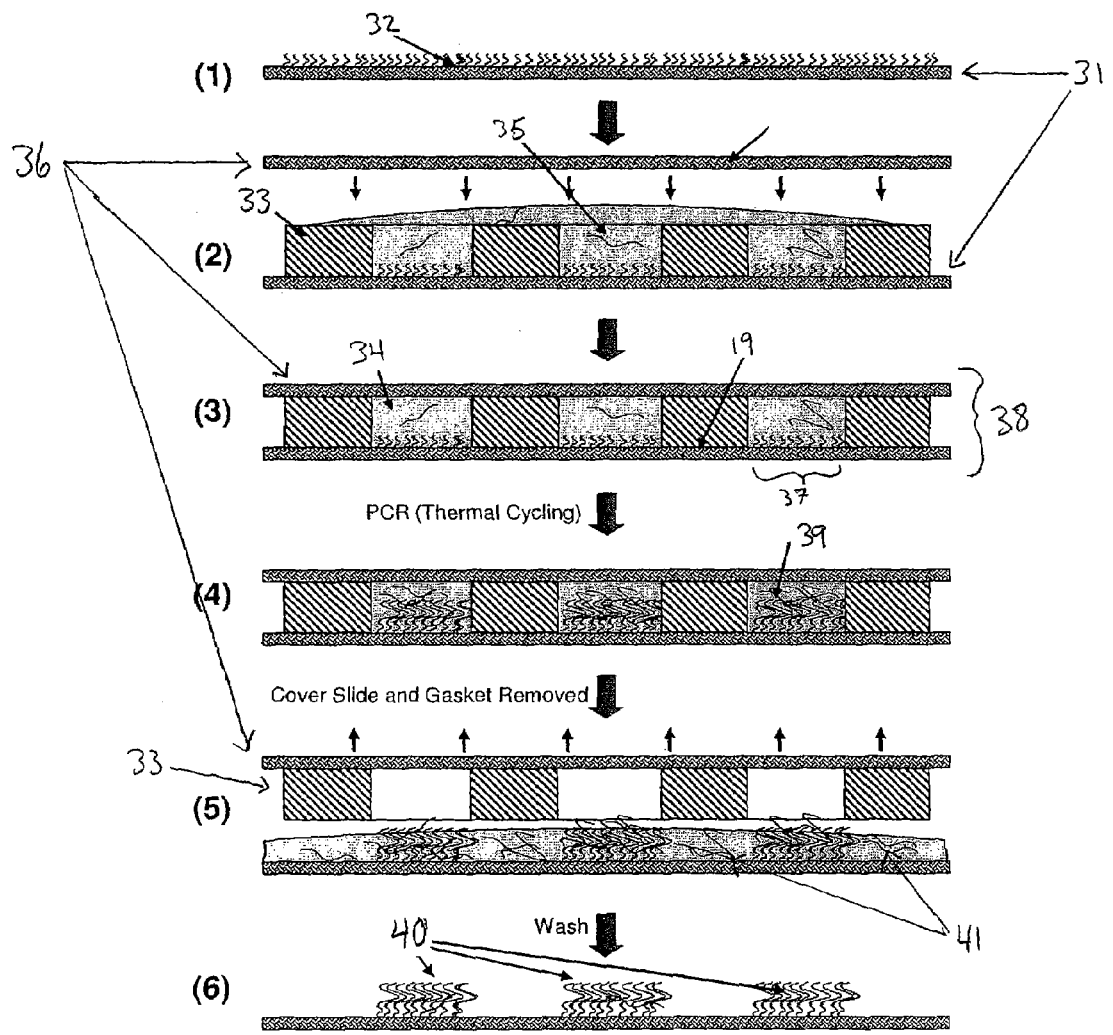

FIG. 3 shows one embodiment of the method of utilizing one embodiment of the device of the present invention to create amplified product.

Figure 4:
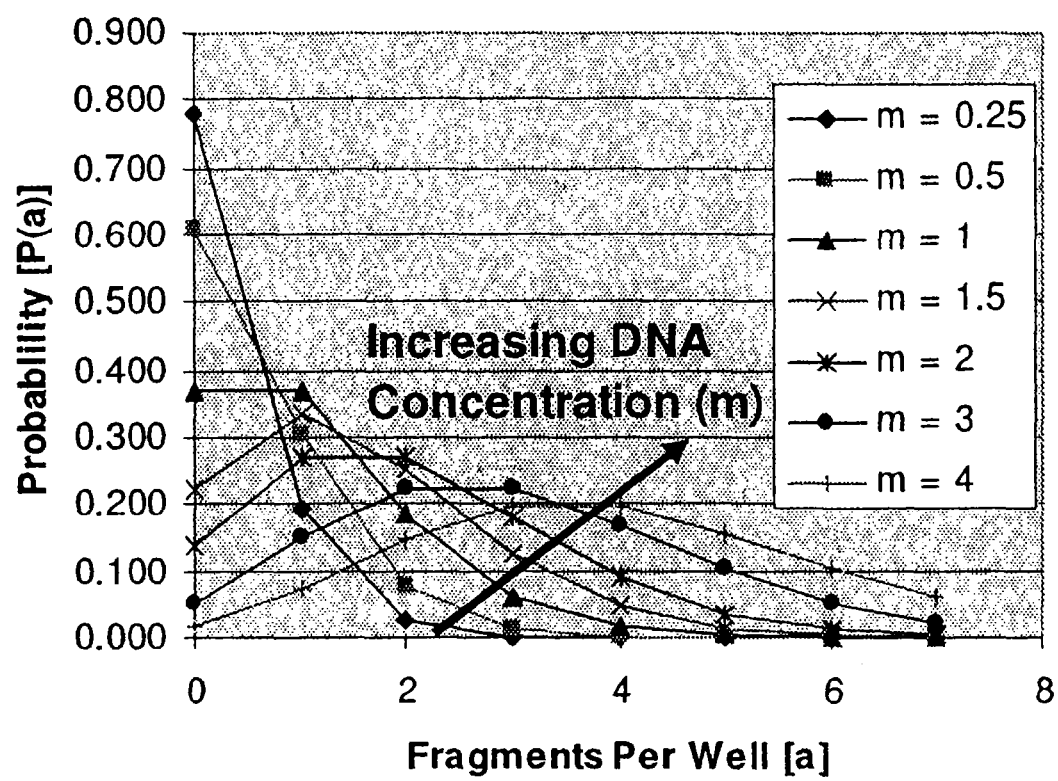

FIG. 4 shows a Poisson probability distribution with varying average molecule densities per well (m).

Figure 5:
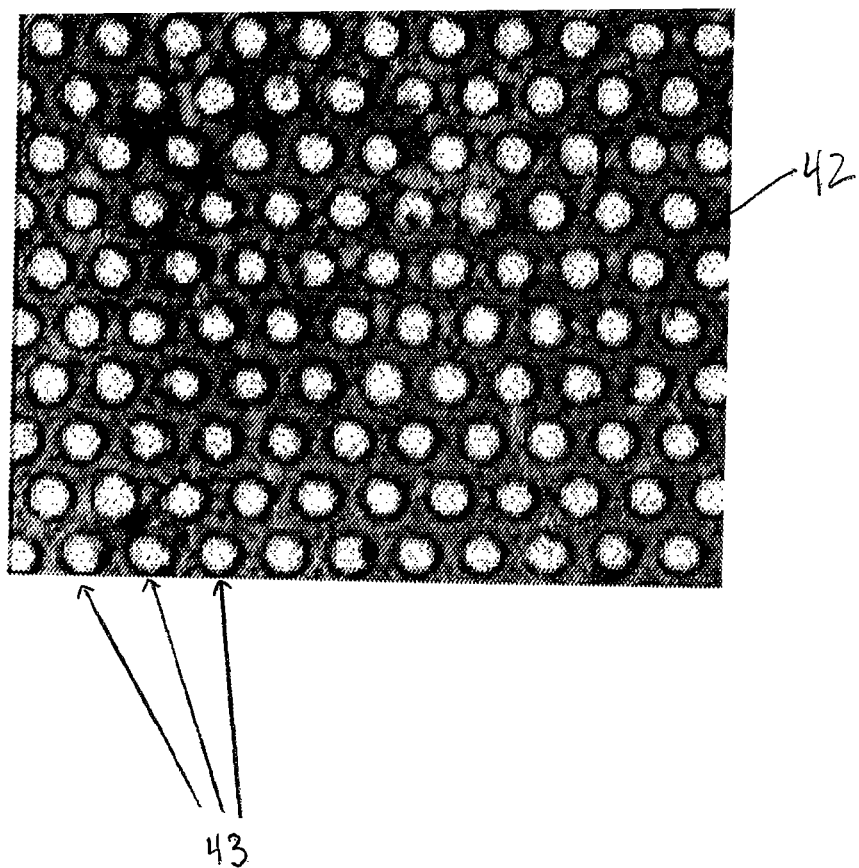

FIG. 5 shows a perforated gasket with 30 micron holes at 50 micron spacing through a 25 micron thick polyimide film.

Figure 6:
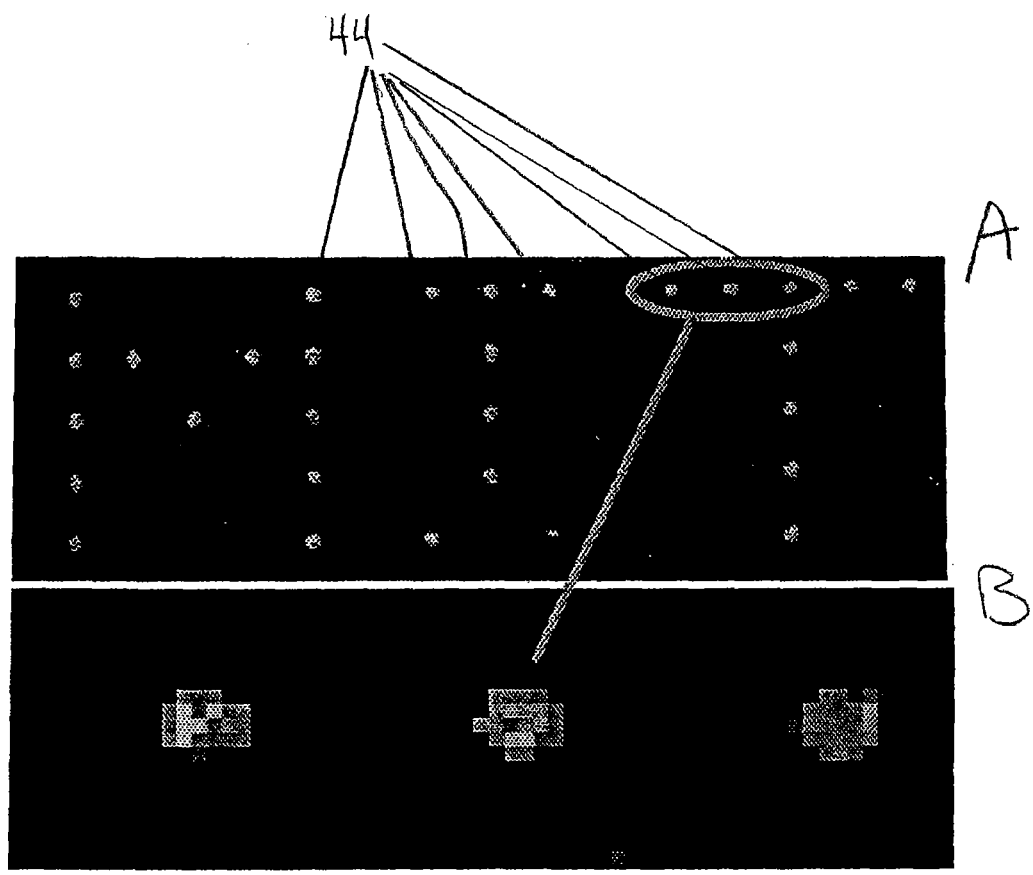

FIG. 6 is a scanned fluorescent image from single base extension reactions on DNA templates bound to the surface of a glass slide using a patterned ("MIT") prototype chip. The integrated chip was formed from a glass slide and a molded PDMS piece that had 40 micron holes at about a 200 micron spacing. The scanner resolution was 5 microns.

Figure 7:
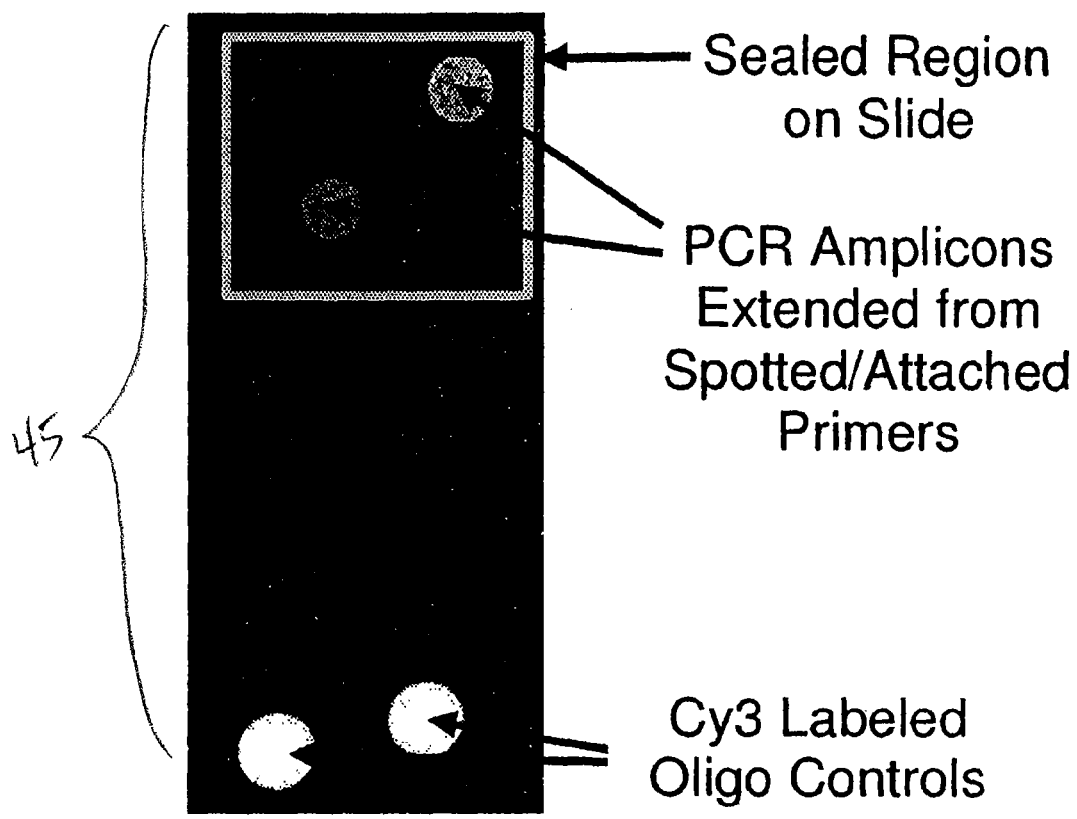

FIG. 7 is a fluorescent scanner image of a glass slide showing PCR amplification of primers bound to a slide.

DESCRIPTION OF THE INVENTION

The present invention relates to methods and devices for amplifying nucleic acid, and, in particular, amplifying so as to generate products on a surface without the use of emulsions. In a preferred embodiment, a plurality of groups of amplified product are generated on the surface, each group positioned in different (typically predetermined) locations on said surface so as to create an array. In one embodiment, each group is homogeneous. In one embodiment, each group consists of amplified product of a single nucleic acid template. In one embodiment, the method comprises performing limiting dilution PCR within closed compartments (e.g. sealed regions) created by two surfaces coming together. Performing a limiting dilution PCR on a surface (e.g. surface of a slide, chip, etc.) rather than in emulsion allows for a simpler and less cumbersome approach. In one embodiment, the present invention contemplates that the device a) isolates each region (e.g. reaction site) from one another and b) contains them for thermal cycling. In one embodiment, the device is disposable.

Figure 1:
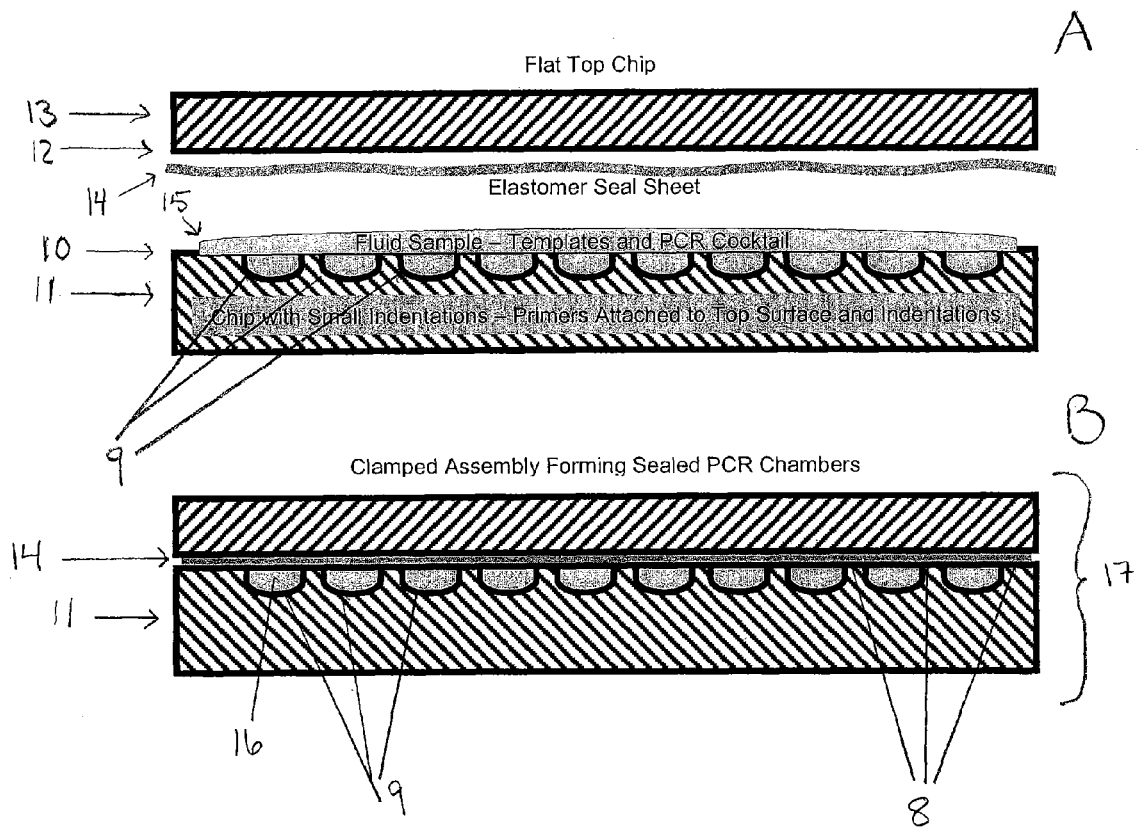
FIG. 1 shows one embodiment of a device for amplification on a surface.

FIG. 1A shows an embodiment wherein the top surface (10) of the bottom piece (11) has a plurality of indentations (9); however, in other embodiments, the bottom surface (12) of the top piece (13) has indentations, or both pieces have indentations. FIG. 1B shows an assembled three piece embodiment (17); however, in some embodiments, the middle piece (14) is eliminated and the bottom surface (12) of the top piece (13) is simply brought into contact with the top surface (10 of the bottom piece (11). This will also cause a portion of the solution (15) to run off the bottom piece (11), although a portion (16) will remain in the indentations (9), i.e. they will be fluid-filled (although they need not be completely filled). The bottom surface (12) of the top piece (13) in this embodiment may or may not have biomolecules (e.g. primers) attached thereto (not shown). Whether the middle piece (14) is used or not, biomolecules on the contact points (8) (i.e. at the interface between the surfaces) will be masked, while biomolecules (e.g. primers) within the indentations (9) will be unmasked and functional. Template in the solution (15) can be diluted to a concentration whereby each indentation (9) on average contains between 1 and 100 molecules, and more preferably, 1 and 3 molecules of template at the point the device is assembled (or, if desired, less than 1 molecule on average).

FIG. 2A shows an embodiment of an assembled three-piece device (20) wherein the primers (21) are only on the top surface (22) of the bottom piece (23). The middle piece (18) masks the primers where it contacts the top surface (22). Once the device is thermocycled and taken apart (FIG. 2B), the result is amplified product (24) in discrete regions (25) on one surface, i.e. one array (26). However, the present invention contemplates embodiments wherein both surfaces comprise primers; for example, the bottom surface (27) of the top piece (28) can also comprise primers (not shown) and the result is amplified product on both surfaces, i.e. two arrays (one being the mirror image of the other). Such arrays can be used for standard biological assays (e.g. hybridization, sequencing, etc.).

FIG. 2A shows a molecule of template (29) suspended in solution. The solution can be diluted to maximize the chance of having one (or a few) starting molecules in each chamber. Template (29) in the solution can be diluted to a concentration whereby each channel (30) on average contains between 1 and 100 molecules, and more preferably, 1 and 3 molecules of template at the point the device is assembled. Or, if desired, the solution can be diluted to maximize the chance of have no more than one starting molecules in each chamber. For example, template (29) in solution can be diluted to a concentration whereby each channel (30) on average contains less than 1 molecule).

While FIG. 2 has been illustrated with reference to primers, other biomolecules are contemplated. For example, enzymes might be attached the bottom surface (or both surfaces) and masked by the middle piece so as to create reaction channels. Substrate could be processed in the channels and the result captured in an array format. Similarly, antibodies, receptors and the like can be similarly arrayed.

FIG. 3 shows one embodiment of the method of utilizing one embodiment of the device of the present invention to create amplified product. Step 1 comprises coating a surface (31) with a biomolecule to create attached biomolecules (32) (e.g. attached primer(s)). Step 2 comprises a) masking a portion of the attached biomolecules (32) using a middle piece (or pieces) at the interface (19) of the coated surface (31) and the middle piece (33), b) leaving a portion of the attached biomolecules (32) unmasked in discrete regions (34) (e.g. channels), and C) introducing a solution (35) comprising unattached biomolecules (e.g. template, polymerase, etc.). Step 3 comprises sealing the channels (34) with atop piece (36) to create sealed regions (37) (e.g. sealed compartments, sealed chambers, etc.) wherein the unmasked attached biomolecules (32) are functional. Step 4 comprises initiating a reaction (e.g. PCR by thermocycling the assembled device (38)) so as to create product (39) (e.g. amplified product from PCR). Step 5 involves taking the assembled device (38) apart, thereby removing the top piece (36) and the middle piece or pieces (33) so as to provide a surface (31) with product (39) in a plurality of discrete regions (40). Step 6 (optional) comprises washing to ensure the removal of all unattached biomolecules (41).

DESCRIPTION OF PREFERRED EMBODIMENTS

In one embodiment, the present invention contemplates using a limiting dilution technique to provide conditions such that PCR products may be generated from a single molecule (i.e., for example, a DNA template or nucleic acid fragment).

By performing the limiting dilution technique prior to the PCR where less than one template molecule on average contacts the indentations (e.g. wells) or channels, most of the wells or channels will contain either a single molecule of DNA or no DNA. Relatively few wells or channels will contain multiple templates. Clearly, a less dilute solution will result in a greater number of template molecules per well (and fewer empty wells). Although it is not necessary to understand the mechanism of an invention, it is believed that the Poisson distribution governs the distribution of fragments in wells:

$$P(a) = e^{-m}\left(\frac{m^a}{a!}\right), \quad (1)$$

where $P(\alpha)$ is the probability of a well having some integer number of molecules (a) based upon a per well average number of available molecules (m). In one embodiment, (m) is equivalent to a specific dilution level. Performing PCR on a set of highly dilute wells will then generate some number of wells with copies of identical molecules and a few other wells with different templates. Indeed, the present invention contemplates in one embodiment methods and devices wherein different template are placed in the same indentation or channel.

For example, a representative Poisson distribution can be generated using a number of values of (m). Changing (m) means that the distribution of the number of molecules per region changes. See FIG. 4. This illustration shows that in order to minimize the number of wells with different templates, a dilution providing an average of 0.25 molecules per well (e.g., m=0.25), generates a library where 2.6% of the wells contain different templates. Consequently, approximately 20% of the wells contain single molecules and approximately 78% of the wells contain no molecules.

In one embodiment, the present invention contemplates providing wells with either a single template or several different templates. One advantage of this embodiment is that a dilution level (m) may be chosen that maximizes the number templates that will be amplified, but does not use too many templates to provide useful results (i.e., for example, more than four). In a preferred embodiment, each well has between 1 and 3 templates on average. To maximize the number of single molecule regions, in one embodiment, the optimal dilution is chosen as m=1 (line with diamonds in FIG. 4).

As just described, limiting dilution may result in any particular well i) being empty; ii) consisting of a single DNA template; or iii) comprising two or more different DNA templates. In the case of a single DNA template, universal primers may be employed to amplify the single molecule to saturation. Although it is not necessary to understand the mechanism of an invention, it is believed that PCR under limiting dilution conditions will start more slowly than a standard PCR assay since it will be more difficult for the polymerase to "find" the single DNA template. It is further believed that it may take up to 60 cycles in a thermal cycler to reach saturation. When two or more different templates are within the same well (i.e., multiplexed) proper PCR conditions are not as predictable. In one embodiment, the present invention contemplates methods wherein a first DNA template is amplified faster than a second DNA template in a multiplexed amplification configuration.

EXPERIMENTAL

Some of the embodiments described above are illustrated below with experimental examples. Of course, such examples are not meant to limit the scope of the claims in any manner.

Example 1

Figure 2:
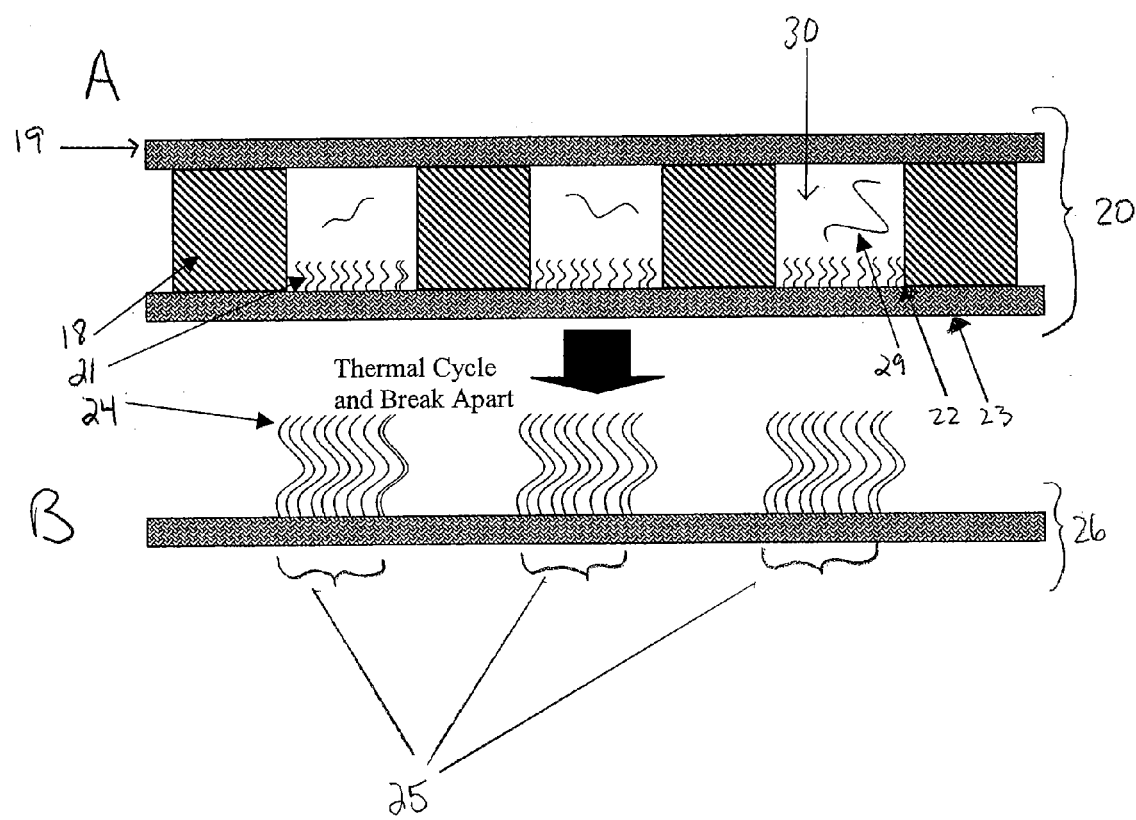
FIG. 2 shows another embodiment, wherein the device is characterized by channels created by top and bottom pieces (without indentations) separated by a third piece (which can be, in one embodiment, a perforated polymeric gasket). FIG.

In this example, the generation of prototype gaskets (for use as a middle piece in one embodiment of the device, see FIG. 2) by laser drilling holes through polymer films is described. Both polyimide and polycarbonate sheets have been employed and thicknesses of both 13 microns and 50 microns have been tested. FIG. 5 shows one embodiment of a prototype gasket fabricated from 25 micron thick polyimide film (42) with 30 micron holes (43) drilled at 50 micron spacing several hundred at a time by an Excimer laser system.

Example 2

In this example, a prototype molded piece of polydimethylsiloxane (PDMS) material was employed which had 40 micron wells as small reaction chambers. The piece was molded using a micromachined silicon wafer as the negative mold for the PDMS. When cured, PDMS is a flexible polymer which is frequently used to create microchannel fluidic systems for a variety of applications. The PDMS piece had a pattern of 40 micron holes at 200 micron spacing. It was clamped against an epoxide activated microarray slide (Corning, Corning, N.Y.) which was covered with a solution of oligonucleotide templates with an amine group on the 5' end and a hairpin on the 3' end (used for extension priming). This entire assembly was left overnight for the amine groups to bond with the epoxy groups. The assembly was then taken apart and a single base extension reaction with labeled nucleotide and Klenow fragment polymerase was performed on the slide. The slide was scanned in a General Scanning ScanArray 4000 scanner (5 micron resolution) and is shown in FIG. 6A. The spots (44) on the chip produced about 100 times the fluorescent signal as the areas which were masked by the PDMS piece. A higher magnification (6B) of a region is also shown.

Example 3

In this example, solid phase PCR is described. The feasibility of device shown in FIG. 2 was demonstrated by performing the reaction in a somewhat larger enclosed chamber on a glass chip. The Corning epoxide glass surface was spotted in two places with a forward PCR primer attached through an amino group at the 5' end. The primer was designed to contain a linker that would allow the primer to be elevated away from the glass surface. The linker structure contained a 5' amino group and two 18 atom hexa-ethyleneglycol linkers. The reverse PCR primer was free in solution and had a fluorescent label at the 5' end. Labeled ten-mer poly-T oligonucleotides were also spotted onto the glass surface outside the reaction chamber with the same linker attachment groups. The reaction chamber was formed around the bound forward primers by a one cm square adhesive gasket and a thin plastic barrier. The PCR reaction solution was added inside the gasket and then sealed, with the barrier. The slide (45) was sandwiched between metal plates and placed onto a Bio-Rad PTC-200 thermal cycler with a heated lid. The entire sandwich was cycled through three temperatures of 95, 50, and 72° C. for 30 cycles. Following the completion of thermal cycling, the sandwich was disassembled and the slide was washed for one hour in PCR buffer and water. It was then dried and imaged on a ScanArray 4000 microarray scanner. The bound, labeled amplicons, FIG. 7, show the PCR reaction was successful.

Example 4

In this example, two surfaces (e.g. glass slides) are used to sandwich a middle piece (e.g. perforated polymeric gasket) and create many small cylindrical compartments for housing PCR reactions (FIG. 3). The perforated film between the slides has potentially millions of holes at close spacing and is about 50 microns thick. The surface of at least one of the slides which faces the gasket has at least one of the PCR primers (forward or reverse, or both) attached to it (FIG. 3, step (1)). The reaction cocktail of templates, primers, dNTPs, polymerase and buffer is added, the gasket is placed over the coated surface, and then the second surface is placed on top of the entire assembly (FIG. 3 steps (2 and 3)). During assembly, any extra fluid is allowed to escape out the sides of the sandwich and the entire assembly is clamped together. The gasket may be treated on one or two sides with an adhesive material to either eliminate the clamping or help to facilitate sealing. The entire secured assembly is then subjected to thermal cycling and PCR amplification occurs in each of the chambers created by the gasket holes and the two slides (FIG. 3 step (4)). At the end of the amplification, a number of amplicons are formed and some are attached to the surface through extension of the primers which were attached to the surface prior to amplification. No amplicons are attached to the primers which are masked by the gasket material (not in the chambers). Thus, when the sandwich is disassembled (FIG. 3 step (5)), the result will be a surface with a plurality of discrete groups comprising DNA amplicon attached in an array of the same pattern as the holes in the gasket which were used (FIG. 3 step (6)). The top glass slide and gasket may also be made from one piece which both provides the chambers for PCR and creates a seal against the bottom slide.

Example 5

As noted above, in one embodiment, both the forward and reverse primers are attached to the same surface. In this embodiment, amplification causes the generation of forward single strands and reverse single strands. In one embodiment, a separate sequencing primer is then used to determine the sequence of the forward single strands; then, a re-priming step with a different sequencing primer is used to determine the sequence of the reverse single strands. In this manner, one can get sequence information from both ends.

In some embodiments, the present invention contemplates, activatable (temporarily inactive) oligonucleotide primers are employed. For example, when the first sequencing primer is used, the second sequencing primer is inactive. In this example, an activatable primer has a phosphorylated 3'-terminal phosphate that prevents the primers from themselves being extended. To activate the primer, the phosphate group is removed by treatment with a phosphatase enzyme, thereby "activating" the primer. One suitable phosphatase enzyme is alkaline phosphatase.

The invention claimed is:

1. A method of amplifying nucleic acid template, comprising:
a) providing:
  i) a first element comprising a first surface;
  ii) a second element comprising a second surface;
  iii) a plurality of indentations, wherein said indentations are formed on said first surface without extending through the entire thickness of said first surface;
  iv) a first solution comprising a plurality of first PCR primers; and
  v) a second solution comprising templates, polymerase, dNTPs and primers, wherein said primers are second PCR primers;
b) contacting said first surface with said first solution under conditions such that at least a portion of said first PCR primers attach to at least a portion of said first surface so as to create a modified surface comprising attached molecules;
c) contacting said modified surface with said second solution;
d) positioning said second surface on top of said modified surface, so as to create a plurality of first regions defined by said indentations and second regions defined by contact of said surfaces, said first regions comprising unmasked attached molecules, and said second regions comprising masked attached molecules, t hereby making a device;
e) thermocycling said device under conditions such that at least a portion of said template is amplified by said unmasked attached molecules.

2. The method of claim 1, whereby said positioning of step d) causes at least a portion of said second solution on said modified surface of said first element to move off of said modified surface and be removed from said modified surface.

3. The method of claim 1, wherein said contacting of step b) results in substantially the entire surface being contacted with said solution.

4. The method of claim 1, wherein said second PCR primers consist of reverse PCR primers.

5. The method of claim 1, further comprising the step f) separating said first element from said second element.

6. A method amplifying nucleic acid template without the use of emulsions, comprising:
a) providing:
  i) a first element comprising a first surface;
  ii) a second element comprising a second surface;
  iii) a plurality of indentations, wherein said indentations are formed on said first surface;
  iv) a first solution comprising a plurality of first PCR primers; and
  v) a second solution comprising templates, polymerase, dNTPs and primers, wherein said primers are second PCR primers;
b) contacting said first surface with said first solution under conditions such that at least a portion of said PCR primers attach to at least a portion of said first surface so as to create a modified surface comprising attached molecules;
c) contacting said modified surface with said second solution;
d) positioning said second surface on top of said modified surface, so as to create a plurality of first regions defined by said indentations and second regions defined by contact of said surfaces, said first regions comprising unmasked attached molecules, and said second regions comprising masked attached molecules, thereby making a device;
e) thermocycling said device under conditions such that at least a portion of said template is amplified by said unmasked attached molecules without the use of emulsions.

7. The method of claim 6, wherein said first element comprises glass.

8. The method of claim 7, wherein said first element is a microscope slide.

9. A method amplifying nucleic acid template without the use of emulsions, comprising:
   a) providing:
      i) a first element comprising a first surface;
      ii) a second element comprising a second surface;
      iii) a plurality of indentations, wherein said indentations are formed on said first surface without extending through the entire thickness of said first surface, said indentations being between 50 nanometers and 50 microns in diameter, and spaced on said first surface at between 1.2 and 2 times the diameter;
      iv) a first solution comprising a plurality of first PCR primers; and
      v) a second solution comprising templates, polymerase, dNTPs and primers, wherein said primers are second PCR primers;
   b) contacting said first surface with said first solution under conditions such that at least a portion of said PCR primers attach to at least a portion of said first surface so as to create a modified surface comprising attached molecules;
   c) contacting said modified surface with said second solution;
   d) positioning said second surface on top of said modified surface, so as to create a plurality of first regions defined by said indentations and second regions defined by contact of said surfaces, said first regions comprising unmasked attached molecules, and said second regions comprising masked attached molecules, thereby making a device; and
   e) thermocycling said device under conditions such that at least a portion of said template is amplified by said unmasked attached molecules without the use of emulsions, wherein said template is not amplified by said masked molecules.

10. The method of claim 9, wherein said first element comprises glass.

11. The method of claim 10, wherein said first element is a microscope slide.

* * * * *